(12) United States Patent
Lehmann

(10) Patent No.: US 7,841,225 B2
(45) Date of Patent: Nov. 30, 2010

(54) MINIATURISED SEPARATION COLUMN WITH BONDING AGENT FOR A GAS CHROMATOGRAPH

(75) Inventor: Uwe Lehmann, Hamburg (DE)

(73) Assignee: SLS Micro Technology GmbH, Hamburg (DE)

( * ) Notice: Subject to any disclaimer, the term of this patent is extended or adjusted under 35 U.S.C. 154(b) by 736 days.

(21) Appl. No.: 11/665,588

(22) PCT Filed: Oct. 17, 2005

(86) PCT No.: PCT/EP2005/011146
§ 371 (c)(1), (2), (4) Date: Aug. 10, 2007

(87) PCT Pub. No.: WO2006/042727
PCT Pub. Date: Apr. 27, 2006

(65) Prior Publication Data
US 2008/0092626 A1    Apr. 24, 2008

(30) Foreign Application Priority Data
Oct. 15, 2004   (DE) .................. 10 2004 050 569

(51) Int. Cl.
*G01N 30/60* (2006.01)
(52) U.S. Cl. .................................. 73/23.39
(58) Field of Classification Search ............. 73/23.35, 73/23.39
See application file for complete search history.

(56) References Cited

U.S. PATENT DOCUMENTS 6,306,200 B1 * 10/2001 Yu .............................. 96/102
6,568,244 B2 * 5/2003 Binz et al. .................... 73/23.2
2003/0233862 A1   12/2003 Wise et al.
2006/0210441 A1 *  9/2006 Schmidt et al. ............... 422/89

FOREIGN PATENT DOCUMENTS

DE      103 01 601       8/2004
WO      WO 01/87768 A2   11/2001

OTHER PUBLICATIONS

Feustel, A. et al., "A Micro Mass Spectrometer," *Sensor Kongressband*, 1995, pp. 465-470.
Feustel, A. et al., "A Microsystem Mass Spectrometer," *Micro Total Analysis Systems*, 1994, pp. 299-304.
Lehmann, U., "Analysis in miniature," *Vacuum Solutions*, Nov./Dec. 1998, pp. 13-15.
Lehmann, U., "Autarky Gas Chromatographic System Realized in MEMS Technology on a Credit Card-Sized Board," *Abstracts Pittcon*, 2005, 180-9.

(Continued)

*Primary Examiner*—Daniel S Larkin
(74) *Attorney, Agent, or Firm*—Saliwanchik, Lloyd & Saliwanchik

(57) ABSTRACT

The invention concerns a separation column in microsystem technology for a gas chromatograph comprising a first substrate, a second substrate which is arranged on the first substrate, wherein a trench structure is provided in at least one substrate and the trench structure is sealed off relative to the environment, a stationary phase applied at least to parts of the trench structure, a gas inlet connected to the trench structure, and a gas outlet connected to the trench structure.

20 Claims, 2 Drawing Sheets

OTHER PUBLICATIONS

Lehmann, U. et al., "A micro gas chromatograph based on a plasma polymerized siliconorganic stationary phase," *Sensor Kongressband II*, 1997, pp. 151-153.

Lehmann, U. et al., "Micro machined analytical gas chromatograph with a plasma polymerised stationary phase," *Sensor Proceedings II*, 2001, pp. 487-492.

Lehmann, U. et al., "Micro machined gas chromatograph based on a plasma polymerised stationary phase," *Micro Total Analysis Systems*, 2000, pp. 167-170.

Lehmann, U. et al., "A Miniaturised Gas Chromatographic Module on a Credit Card Sized Motherboard," *Sensor Proceedings*, 2003, pp. 157-161.

Lehmann, U. et al., "A miniaturized gas chromatograph for autonomous and longtime measurements," *Sensor Proceedings I*, 1999, pp. 155-158.

Lehmann, U., "A Packed Column Realized on a 1 $cm^2$ Sized Silicon Glass Chip for Permanent Separation," *Abstracts Pittcon*, 2005, 1910-5P.

Lehmann, U., "World's Smallest, Self-Sufficient Gas Chromatography Module from SLS Micro Technology," *Abstracts Pittcon*, 2004, 1100-100.

"Small is Beautiful," *The Column*, Jul. 2005, pp. 22-23.

Petzold, G. et al., "A Micro Mass Spectrometer," *Micro Total Analysis Systems*, 2001, pp. 224-226.

Siebert, P. et al., "Processing of Complex Microsystems: A Micro Mass Spectrometer," *Symposium on Design, Test, and Microfabrication of MEMS and MOEMS*, Mar.-Apr. 1999, vol. 3680, pp. 562-571.

Siebert, P. et al., "Surface microstructure/miniature mass spectrometer: processing and applications," *Appl. Phys. A*, 1998, vol. 67, pp. 155-160.

Noh, H., et al., "Parylene Gas Chromatographic Column for Rapid Thermal Cycling" *Journal of Microelectromechanical Systems*, Dec. 2002, pp. 718-725, vol. 11, No. 6.

Schnell, A. R., et al., "Using the Compromise Decision Support Problem in Microsystem Design: A Formulation for a Miniature Parylene Gas Chromatographic Column" *Proceedings of DETC'04 ASME 2004 Design Engineering Technical Conferences and Computers and Information in Engineering Conference*, Sep. 28-Oct. 2, 2004, pp. 1101-1109, vol. 1.

\* cited by examiner

MINIATURISED SEPARATION COLUMN WITH BONDING AGENT FOR A GAS CHROMATOGRAPH

CROSS-REFERENCE TO A RELATED APPLICATION

This application is a National Stage Application of International Application Number PCT/EP2005/011146, filed Oct. 17, 2005; which claims priority to German Application No. 10 2004 050 569.1, filed Oct. 15, 2004.

BACKGROUND OF THE INVENTION

The invention concerns a separation column in microsystem technology for a gas chromatograph comprising a first substrate, a second substrate which is arranged on the first substrate, wherein a trench structure is provided in at least one substrate and the trench structure is sealed off relative to the environment, a stationary phase applied at least to parts of the trench structure, a gas inlet connected to the trench structure, and a gas outlet connected to the trench structure. A further aspect of the invention is a process for the production of a separation column comprising the steps: forming a trench structure in a first substrate, preferably a silicon wafer, applying a stationary phase to at least one portion of the trench structure, preferably by means of polymerisation of a liquid starting material, and sealing off the trench structure by applying a second substrate, preferably a silicon or glass wafer, to the first substrate. Finally a further aspect of the invention is the use of a gas chromatograph in specific areas of use.

Gas chromatographs have been used for some time in chemical laboratories for the analysis of unknown substances and compositions of substances. A new development in the field of gas chromatography is represented by miniaturised separation columns and miniaturised gas chromatographs, as are described for example in patent specifications DE 197 26 000 C2 and DE 103 01 601 B3. Those separation columns and gas chromatographs which are produced using microsystem technology have the considerable advantage that analysis is possible with very small measurement volumes and the entire gas chromatograph is of a very compact structure.

In the case of the miniaturised separation columns an essential feature of the separation column or the separation column production process is that the stationary phase is applied in the form of a layer which is as thin as possible and distributed as uniformly as possible in the separation column. In that respect the problem generally arises that the stationary phase does not achieve adequate mechanical adhesion in the separation column and thus parts of the stationary phase come away spontaneously or during later use of the gas chromatograph. That results in falsification of the measurements and also measurement inaccuracies.

A further problem with miniaturised separation columns in microsystem technology is that the base material of the separation column, that is to say usually the substrate material, has an electrostatic influence which influences the measurement and adversely impairs measurement accuracy. That influence is frequently to be attributed to polarities in the substrate and/or the stationary phase.

Finally a further problem is that the mechanical adhesion of the stationary phase in the separation column diminishes during the operating period of the gas chromatograph and that electrostatic influences of the substrate and/or the stationary phase increase during the operating period. The consequence of this is that the service life of the known separation columns is limited by virtue of the reduction in separation efficiency of the separation column and by virtue of the increase in measurement inaccuracies.

SUMMARY OF THE INVENTION

The object of the invention is at least to reduce one of the above-mentioned problems and in the best-case scenario completely eliminate same.

In a separation column as set forth in the opening part of this specification that object is attained by a bonding agent which is at least partly arranged between the walls of the trench structure and the stationary phase.

The bonding agent according to the invention improves the mechanical adhesion of the stationary phase in the separation column insofar as it provides a higher level of adhesive binding force to the substrate on the one hand and to the stationary phase on the other hand, than the adhesive binding action between the stationary phase and the substrate material without bonding agent. The cohesive binding forces within the bonding agent are also greater than the adhesive forces between the stationary phase and the separation column material of conventional separation columns. That provides a substantial improvement in the adhesion of the stationary phase in the separation column.

Furthermore electrostatic passivation can be achieved by the bonding agent so that a substantially nonpolar layer is provided on the substrate prior to the application of the stationary phase. In that way it is possible on the one hand to achieve protection for the substrate material from the mobile phase, that is to say the analysis and carrier gas, and in addition it is possible to achieve an almost completely non-polar stationary phase which retains those desired nonpolar properties even over a long operating period of the separation column.

The separation column which is developed in accordance with the invention thus permits a prolongation of the service life by virtue of a substantial reduction in the decrease in separation efficiency as a consequence of the improved mechanical bonding effect and electrostatic passivation of the stationary phase.

The trench structure in the substrate can be for example in the form of a double spiral, as disclosed in DE 197 26 000 C2, FIG. 1 thereof. In particular a meander-shaped configuration of the separation column is also advantageous which is as described in Lehmann, U: Micromachined analytical gas chromatograph with a plasma polymerized stationary phase, Proceedings Sensor 2001, Vol 2, pages 487-492. In that case either the trench structure can be respectively provided in a substrate and the second substrate can be connected as a cover plate to that substrate or corresponding trench structures can be provided in both substrates which are then joined together in such a way that the two trench structures join to form a passage which forms the separation column.

In a first advantageous development of the separation column according to the invention the gas inlet and/or the gas outlet is provided by means of glued-in gas capillaries. That makes it possible to introduce the mobile phase by way of a structure with a very small dead volume so that the level of measuring accuracy is increased.

In that respect it is preferred if the gas capillary is fixed, in particular glued, at least in a trench portion which is enlarged in size with respect to the rest of the trench structure and in which the bonding agent is applied. The bonding agent can thus afford an increased adhesive force. That is achieved in particular if no stationary phase is applied in the region of the adhesive location.

It is particularly advantageous if the bonding agent extends over all the walls defining the trench structure. This means that on the one hand the walls which are provided in the first substrate and which define the trench are advantageously coated with the bonding agent and on the other at least those surface portions of the second substrate which close the trench structure are also coated with bonding agent. In that way, the positive action of the bonding agent is achieved over the entire region of the separation column and the service life of the separation column can be substantially extended.

It is also advantageous if the stationary phase extends over all the walls defining the trench structure or structures. In that way the overall length of the separation column formed by the trench structure is used for the analytical separation action. In that case the stationary phase can advantageously extend over the entire region of the separation column with the exception of those portions at the beginning and end of the separation column, in which the connecting connections required for the gas inlet and the gas outlet are fixed.

In particular it is advantageous if the first and/or the second substrate is a silicon wafer or a glass wafer. Silicon makes it possible to use per se known manufacturing processes for the production of the trench structure. Thus for example it is possible to use the processes of wet-chemical etching, photolithographic masking and plasma etching in order to produce the geometrical structures in the silicon wafer. If a glass wafer is used as the second substrate the join between the silicon wafer and the glass wafer can advantageously be achieved by an anodic bonding operation.

It is further preferable if the bonding agent is adapted to cause at least partial and preferably complete electrostatic passivation of the substrate surface in the region of the trench structure. In that way it is possible to afford a preferably completely nonpolar stationary phase which is advantageous for many analysis purposes. Electrostatic passivation is achieved for many substrate materials by using a completely nonpolar material as the bonding agent. In that respect it may be advantageous in certain situations of use for the bonding agent to be formed by two or more layers of different materials. One of the layers can then be particularly advantageous for mechanical bonding to the substrate material, one of the layers can be particularly advantageously appropriate for electrostatic passivation and one of the layers can be particularly suitable for mechanical bonding to the stationary phase. It is often advantageous for two of those functions or all three functions to be combined in a single material.

Preferably the bonding agent includes an inorganic material. That Inorganic material can be for example a metal or a metal alloy. A number of ceramic materials and mixtures of various Inorganic materials can also be used as the bonding agent.

Preferably the bonding agent includes a nonpolar material. In many cases that makes it possible to provide for electrostatic passivation in a simple fashion.

A further advantageous embodiment is characterised in that the bonding agent includes a first layer portion and a second layer portion. In that case the first layer portion can be adapted in particular for adhesion to the substrate material and the second layer can be suitable for electrostatic passivation.

A further aspect of the invention is a gas chromatograph with a separation column as described hereinbefore. That gas chromatograph is distinguished by the advantages according to the invention of an increased service life and improved separation efficiency and precision.

The gas chromatograph according to the invention can be developed by an injector using microsystem technology comprising a first injector substrate with gas guide passages and a second injector substrate which is movable relative to the first injector substrate and having gas guide passages. In that case the injector can preferably be of the design configuration as described in DE 103 01 601 B3, in particular paragraphs [0024]-[0027] thereof as well as FIGS. 5, 6 and 7 thereof with the related description at paragraphs [0039]-[0041]. Preferably the injector is designed as set forth in that patent specification.

In the above-mentioned embodiment it is advantageous if the first injector substrate is arranged on a circuit board on which the first substrate of the separation column is arranged at the same time. In that fashion on the one hand manufacture of the gas chromatograph according to the invention and in particular the formation of the gas guide passages is simplified while in addition it provides for a particularly compact design configuration.

The gas chromatograph according to the invention can be further developed by a detector using microsystem technology, in particular a thermal conductivity detector, including a gas guide passage provided in a first detector substrate. The detector can be in particular in the form of a thermal through-flow sensor as described in DE 199 06 100 C2, In particular FIGS. 1 and 2 thereof with the related description at paragraphs [0009]-[0011]. Preferably the detector is designed as set forth in the above stated patent specification.

In that respect it is advantageous if the first detector substrate is arranged on a circuit board on which the first substrate of the separation column is arranged at the same time. As described hereinbefore, that in turn simplifies manufacture of the gas chromatograph in particular the provision of the gas guide passages, and achieves a compact structure. In particular it is advantageous if both a first injector substrate and also a first detector substrate are arranged on the circuit board on which the first substrate of the separation column is arranged at the same time.

A further advantageous embodiment is characterised by an electronic control and evaluation unit. That can serve inter alia to control injection of the gas to be analysed and to evaluate the data detected by means of the detector. The electronic control and evaluation unit can also be connected to a storage device or can include such a storage device for the storage of comparative data which serve for evaluation of the data ascertained with the detector.

In that respect it is particularly advantageous if the electronic control and evaluation unit is arranged on a circuit board on which the first substrate of the separation column is arranged at the same time. That provides for a particularly robust and compact arrangement of the electronic components and the separation column. That embodiment is advantageous in particular when the injector and/or the detector are also arranged on the circuit board on which the first substrate of the separation column is arranged at the same time. This embodiment provides that all electronic, fluidic and mechanical components which are essential for the gas chromatograph are combined on a common circuit board and that therefore provides for particularly simple and inexpensive manufacture as well as a robust design.

It is further advantageous in the aforementioned embodiment if there is provided at least one further circuit board which is preferably arranged in parallel spaced relationship with the first circuit board. A separation column can be arranged on that further circuit board, which in terms of the geometry and/or the properties of the stationary phase differs from the separation column on the first circuit board in order thus for example to be able to analyse other substances. The further circuit board can alternatively or additionally have a detector differing from the detector of the first circuit board, for example a more sensitive or a less sensitive detector than the first circuit board, in order in that way to achieve more precise quantitative analyses in a given selected range of substances or quantitative analyses in a broader range of substances. In that way differentiated evaluation can be implemented, for example in accordance with different criteria, in particular in accordance with different substances, on the further circuit board. In that case the additional circuit boards can be added to the main circuit board for example in the form of plug-in units so that this provides a gas chromatograph which can be built up in a modular fashion.

A further aspect of the invention is a portable gas chromatograph, comprising a gas connection connected to an injector for feeding a gas to a separation column; a carrier gas container connected to the separation column; an energy storage means for storing the energy required for operation of the gas chromatograph; an electronic control and evaluation unit, and an output unit for outputting the analysis data ascertained by the evaluation unit; and having a gas chromatograph comprising a first substrate; a second substrate which is arranged on the first substrate, wherein a trench structure is provided in at least one substrate and the trench structure is sealed off relative to the environment; a stationary phase applied at least to parts of the trench structure; a gas inlet connected to the trench structure; a gas outlet connected to the trench structure, and a bonding agent which is at least partly arranged between the walls of the trench structure and the stationary phase, characterized in that the bonding agent is adapted to effect an at least partial electrostatic passivation of the substrate surface in the region of the trench structure. By virtue of the good mechanical connection of the stationary phase to the separation column wall the separation column according to the invention is particularly well suited for use in a portable gas chromatograph as the shocks acting on a portable gas chromatograph have no adverse effects on the separation column according to the invention or smaller adverse effects thereon than on conventional separation columns. In addition the separation column according to the invention is particularly well suited for portable gas chromatographs for the reason that it consumes only a very small amount of carrier gas for an analysis operation so that a carrier gas container of a volume of about half a liter, at the usual bottle pressure of about 200 bars, is already sufficient for several thousand measuring procedures. In that case the energy storage means can preferably be provided in the form of a battery or an accumulator, the output unit can be provided for example in the form of a display or monitor screen or it can be in the form of a data interface for the connection of an electronic storage unit or an external display device.

In that respect it is particularly advantageous if the portable gas chromatograph is designed with the features as generally described hereinbefore with reference to a gas chromatograph.

The underlying object of the invention is further attained by a process of the kind set forth in the opening part of this specification, in which a bonding agent is applied to at least parts of the trench structure prior to the application of the stationary phase. In that case a single material can be applied as a single-layer bonding agent or a plurality of materials can be applied in a plurality of layers in succession as the bonding agent. A development of the process according to the invention can provide that the bonding agent and the stationary phase are applied to the entire trench structure. That development provides for good separation efficiency of the separation column and at the same time ensures secure adhesion and electrostatic passivation over the entire region of the separation column.

It is particularly advantageous if the bonding agent is formed by means of polymerisation of a liquid starting material. That process is preferred inter alia for the reason that chemical polymerisation from the liquid phase is also a preferred process for application of the stationary phase and consequently the bonding agent and the stationary phase can be applied with the same process in that way.

It is further advantageous if the bonding agent and/or the stationary phase is applied by means of physical or chemical deposition out of the gaseous phase (PVD: physical vapor deposition or CVD; chemical vapor deposition), in particular by means of plasma-aided deposition. A large number of different materials can be applied by means of the PVD process or the CVD process so that a wide range of bonding agent substances and stationary phases can be applied with those processes. It is preferable for a cleaning step to take place between the application of the bonding agent and the application of the stationary phase, in particular a plasma cleaning operation or backsputtering. That cleaning step ensures the required purity for the bonding agent, the stationary phase and the transition between the bonding agent and the stationary phase in order in that way to achieve the required analysis accuracy. That development is advantageous in particular when the bonding agent and the stationary phase are applied with different processes so that there is a fear of contamination between the application of the two layers.

It is particularly preferred if the bonding agent and the stationary phase are applied by means of an identical process. That allows a contamination-free succession of the two application processes so that on the one hand it is possible to avoid impurities and consequently a cleaning step is not required.

In that respect it is particularly advantageous if the bonding agent and the stationary phase are applied in a controlled atmosphere, in particular in a vacuum or an inert gas atmosphere, and if that atmosphere remains substantially unaltered between the beginning of the application of the bonding agent and the end of the application of the stationary phase. With that development of the process, either an identical atmosphere can be maintained during the entire application procedure for the bonding agent and the stationary phase or the application of the one material can take place in a first controlled atmosphere, for example a vacuum, and the application of the second material can take place in a second controlled atmosphere, for example an inert gas atmosphere.

A further aspect of the invention are uses of a gas chromatograph.

The use of gas chromatographs is limited at the present time to the area of chemical laboratories. It is known to take samples at locations which are relevant for analysis and for those samples subsequently to be analysed in a chemical laboratory. That procedure suffers from the disadvantage that there is a long period of time between sampling and analysis result. No analysis is possible in real time or quasi-real time. It has been found that the known procedure suffers from a further serious shortcoming in that a loss of substance occurs during transport, for example due to diffusion processes through the wall of the transport container.

It has been found that a more comprehensive and faster analysis of chemical substances, in particular gases and liquids, is required in particular by virtue of intensified environmental regulations and by virtue of the large number of substances processed in manufacturing industry and the emissions which occur in that situation. Furthermore in a series of applications it is necessary, for health purposes, to implement air analysis procedures quickly and regularly, often virtually in real time. Those demands cannot be met with the known use technology.

The invention remedies that problem on the one hand with a use of a gas chromatograph, in particular a gas chromatograph as described hereinbefore, for monitoring and/or analysing air that people breathe, in particular at the workplace, in medical diagnostics and in personal security and disaster control. In particular a miniaturised gas chromatograph and more particularly the gas chromatograph according to the invention is suitable for that use as its compact and robust structure allows reliable monitoring or analysis of the air that people breathe.

That use can occur in particular in endangered regions as in underground mining and in the field of firefighting. In a further use of that kind a gas chromatograph, in particular a gas chromatograph as described hereinbefore, can be employed to monitor the air in the region of electrical installations in order in that way to detect substances which are given off in the initial stage of electrical cable overheating. Those substances can be liberated into the air for example from the insulation of cables, in particular in transformer windings, due to chemical or physical changes, and the detection thereof thus permits early recognition of rises in cable temperature or the beginning of cable overheating and can thus be used to afford protection from cable fires in electrical installations or to detect the operating state of such electrical installations.

The breathing air monitoring procedure according to the invention can also be implemented in the form of regularly monitoring workplaces for health-endangering substances. In addition breathing air monitoring and analysis can be employed for use in mobile or stationary warfare agent detection. Finally further areas of involvement for the use according to the invention for breathing air monitoring are building-chemical assessment and noxious matter and pollutant measurement in the case of furnishing items such as pieces of furniture or carpets, in particular in regard to allergy prevention. In that respect, by virtue of its compact nature and its rapid analysis procedure, a gas chromatograph and in particular the miniaturised gas chromatograph as described hereinbefore permits simple use, even in the private area and can already be employed in the preliminary stages, for example when purchasing furnishing items or other products, for detecting known pollutants and risk-inducing substances.

Finally a further field of use for breathing air monitoring is the analysis of the gases people breathe (supplied and exhaled air), in particular in the case of patients undergoing intensive medical care, for example for diabetes detection or for controlling drug administration.

A further use according to the invention of the gas chromatograph, in particular the gas chromatograph according to the invention, is for monitoring and/or analysing immissions or emissions. Particularly in the course of the required checking of pollutant discharge by manufacturing operations the direct monitoring and analysis of emissions at the location at which the pollutants are introduced into a drain system, into the air or a body of water is increasingly gaining in significance. That monitoring operation can be implemented in particular by miniaturised gas chromatographs as they can rapidly process even very small analysis amounts and are thus suitable for use on site. Furthermore, particularly in the area of regions which are at risk, the gas chromatographs according to the invention make it possible to effect particularly efficient and inexpensive monitoring of the air quality in the region of the consumers.

Furthermore a gas chromatograph, in particular a miniaturised gas chromatograph, can be used for monitoring and/or analysing energy carriers, in particular combustible gases. That use permits on the one hand decentral calorific value monitoring of energy carriers, for example natural gas, and can be employed for example for billing the delivered calorific value amount. Furthermore that application can also be employed in the region of the feed of energy carriers, for example from biogas installations, in order to monitor the quality of the gas which is fed and to permit billing on the basis of the supplied amount of energy.

A further use for a gas chromatograph, in particular a miniaturised gas chromatograph, is monitoring and/or analysing raw materials for the processing industry, in particular foodstuff raw materials for the food industry. When that use is involved, quality assurance of supplies of raw materials can be effected in a simple fashion and can be ensured at an early time in the processing procedure in such a way that the raw material is suitable for the desired production. Furthermore, for example in the case of foodstuff raw materials, qualitative detection of the properties of the raw material can be effected by gas-chromatographic analysis and adaptation of the composition or adaptation of the mixing ratios of various raw materials can be effected on the basis of the data obtained in that way.

Furthermore a gas chromatograph, in particular a miniaturised gas chromatograph, can be used for monitoring and/or analysing processes, in particular fermenting, cooking, baking or roasting processes. With miniaturised gas chromatographs that can be effected even in the consumer area so that monitoring of the processes can be effected for example in privately or industrially employed microwaves or baking ovens.

Finally a further use according to the invention of a gas chromatograph, in particular a miniaturised gas chromatograph, is the analysis of substances with smell. That can be effected on the one hand in the area of scent design, for example perfumes, soaps and other body care agents, cleaning agents and foodstuffs. Furthermore that use is advantageous for a large number of products in respect of which a pleasant scent is desired, for example in buildings, vehicles, in relation to articles of furniture and other furnishing items, articles of clothing or similar.

BRIEF DESCRIPTION OF THE DRAWINGS

Preferred embodiments of the invention are described with reference to the Figures in which.

DETAILED DESCRIPTION

Figure 1:
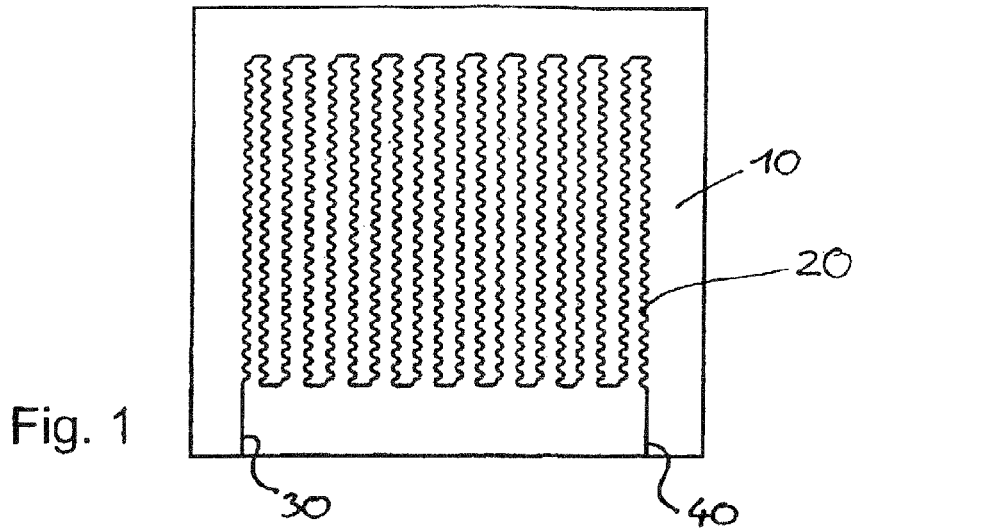
FIG. 1 shows a diagrammatic plan view of a separation column according to the invention.

FIG. 1 shows a main substrate 10 in which a trench 20 of a meander configuration is formed by a wet-chemical etching process. The trench 20 forms the separation column and is connected at a first end to a gas inlet 30 and at a second end to a gas outlet 40.

Figure 2:
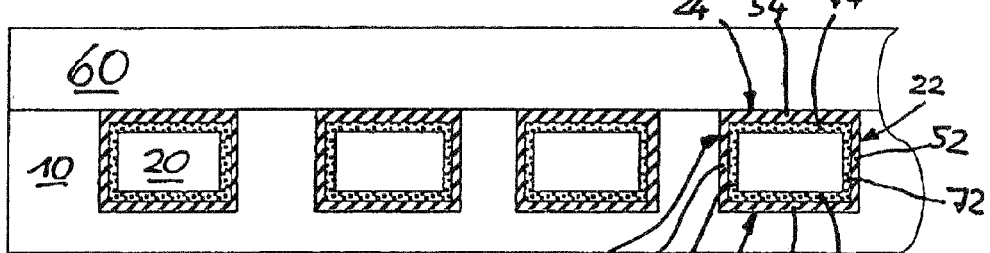
FIG. 2 shows a diagrammatic side view in cross-section of the separation column of FIG. 1.

Referring to FIG. 2, shown therein is a cross-sectional view of the substrate shown in FIG. 1, a reduced number of trenches being shown in the cross-section for reasons of enhanced clarity. The main substrate 10 has a trench 20 which is cut in a plurality of cross-sections. The side walls 21, 22 of the trench and the bottom 23 of the trench are coated with a bonding agent layer 51, 52, 53 which is applied to the first substrate 10. The top side 24 of the trench is coated with a bonding agent layer 54 applied to a second substrate 60.

The cross-section of the trench shown in FIG. 2 is rectangular. In certain embodiments it is advantageous for the corners between the side wall 21 and the bottom 23 and the corner between the side wall 22 and the bottom 23 to be of a rounded-off configuration.

A stationary phase 71-73 is applied to the bonding agent layers 51-53 and a stationary phase layer 74 is applied to the bonding agent layer 54. In that way the walls defining the trench are completely lined with a bonding agent layer 51-54 and a stationary phase 71-74 applied to the bonding agent layer.

Figure 3:
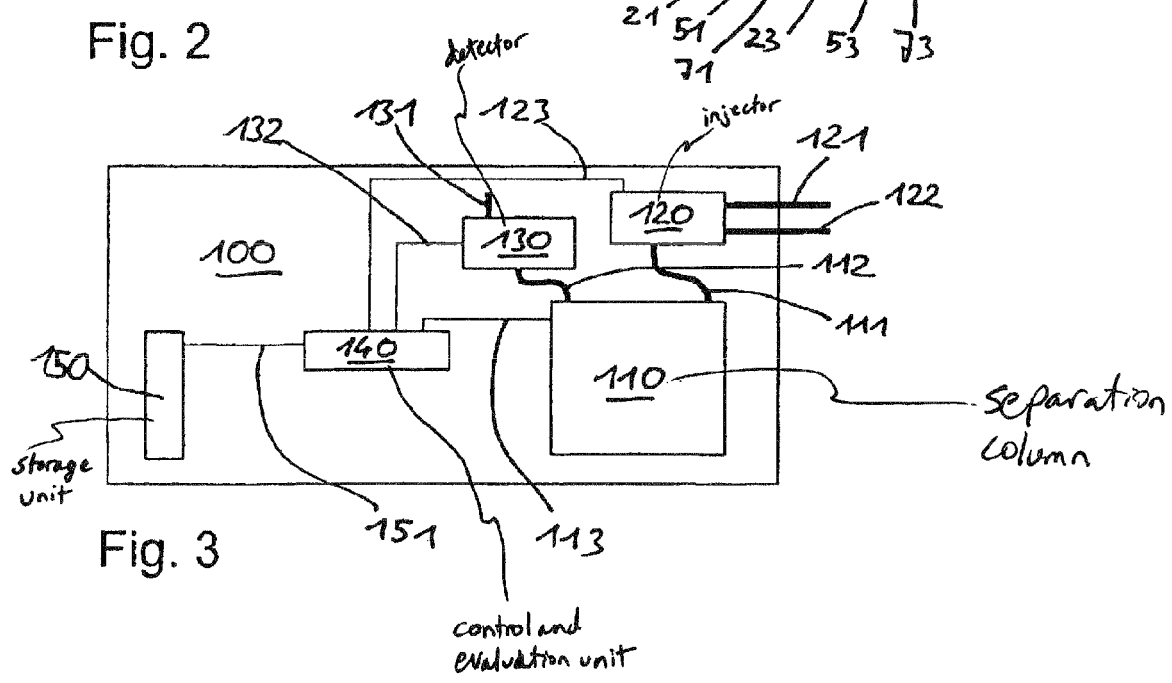
FIG. 3 shows a plan view of a diagrammatic structure of a miniaturised gas chromatograph according to the invention.

Referring to FIG. 3 shown therein is a circuit board 100 which serves as a carrier substrate for a separation column 110 formed thereon. The separation column 110 is connected by way of a line 111 to an injector 120 into which a gas to be analysed and a carrier gas can be introduced by means of two gas feed lines 121, 122. The other end of the separation column is connected by way of a gas line 112 to a detector 130 which analysis the gas issuing from the separation column and thereafter discharges it into the environment by way of a disposal line 131.

The separation column is connected by way of an electric line 113 to a control and evaluation unit 140 for temperature regulation of the separation column.

The injector 120 is connected by way of an electric line 123 to the control and evaluation unit 140 which controls the injector and thus provides for a metered feed of the gas to be analysed, to the separation column. The temperature of the injector is further regulated by way of the electric line. The detector 130 is connected to the control and evaluation unit 140 by way of an electric line 132 in order to process the signals detected by the detector to afford result data and in order to regulate the temperature of the detector.

A storage unit 150 is connected to the control and evaluation unit by way of an electric line 151. Reference data of known substances are stored in the storage unit 150 and can be compared to the data detected by the detector 130 in order to provide qualitative and quantitative Information about the composition of the gas to be analysed.

Figure 4:
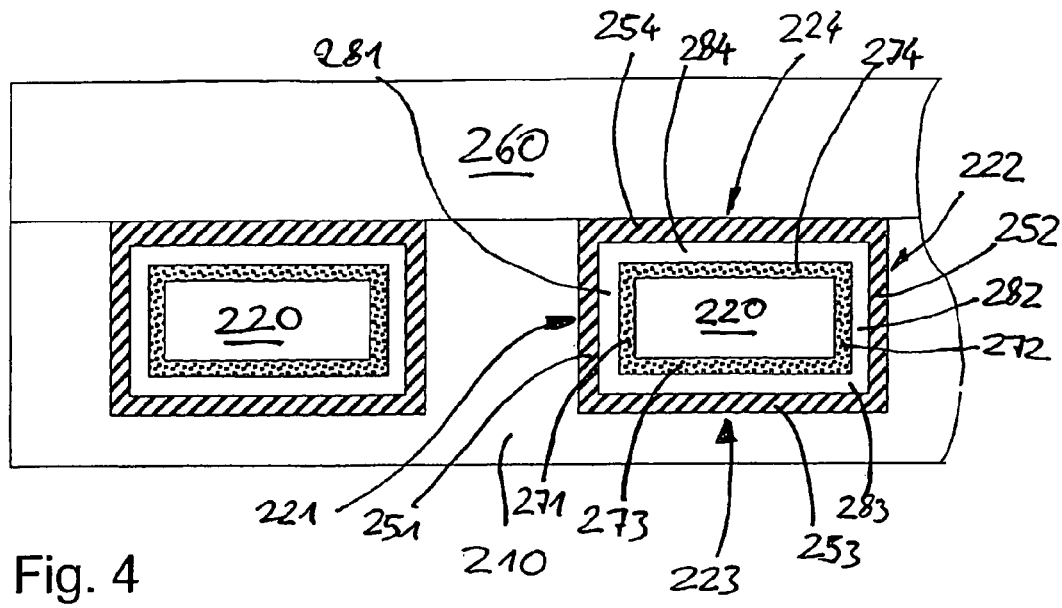
FIG. 4 shows a diagrammatic side view in cross-section as shown in FIG. 2 on an enlarged scale of a separation column according to the invention with a bonding agent layer comprising a plurality of layer portions.

FIG. 4 shows a second embodiment of the separation column according to the invention. A reduced number of trenches is also shown in cross-section in this view for the sake of enhanced clarity. Like the embodiment shown in FIG. 2 the main substrate 210 has a trench 220 which is cut in a plurality of cross-sections. A first layer portion 251, 252, 253 of a bonding agent layer is applied to the side walls 221, 222 of the trench and the bottom 223 of the trench. That first layer portion is of a material which is particularly well suited to adhesion to the substrate material of the main substrate 210.

A second layer portion 281, 282, 283 is applied to the first layer portion of the bonding agent layer. The material of that second layer portion is particularly suitable for electrostatic passivation and adheres with sufficient strength to the first layer portion 251-253 of the bonding agent layer.

Finally, a stationary phase layer 271-273 is applied to the second layer 281-283 so that the second layer portion 281-283 is between the stationary phase 271-273 and the first layer portion 251-253.

A first layer portion 254, a second layer portion 284 of the bonding agent layer and a stationary phase layer 274 are applied to a second substrate 260 in the same sequence, on the top side of the trench 224.

Figure 5:
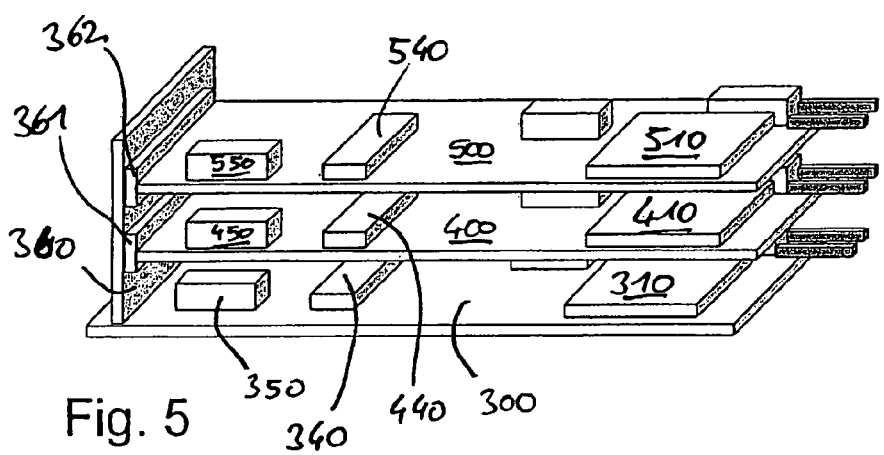
FIG. 5 shows a gas chromatography module according to the invention with a plurality of gas chromatography circuit boards.

FIG. 5 shows a multi-circuit board gas chromatography module in which the components of FIG. 3 are arranged on a main circuit board 300 so that a complete gas chromatography unit is formed on the main circuit board 300.

A circuit board plug-in module 360 is also arranged on the main circuit board 300. The module 360 has two plug connections 361, 362, into each of which a respective additional circuit board 400, 500 is plugged. The additional circuit boards 400, 500, in the same fashion as the main circuit board 300, has all components required for gas chromatography measurement, as shown in FIG. 3.

The circuit boards 300, 400, 500 are electrically connected together by way of the circuit board plug-in module 360 so that the control and evaluation units 340, 440, 540 can communicate with each other and matched control and evaluation can be effected.

In certain embodiments it is also advantageous if control and evaluation is effected centrally on only one of the circuit boards and thus the control and evaluation units on the other circuit boards can be eliminated. In the same manner, the reference data in respect of the individual substances which are matched to the geometry and the stationary phase of the respective separation columns 310, 410, 510 can be stored in only one single storage unit 350 and in that way it is possible to dispense with the storage units 450, 550.

The invention claimed is:

1. A separation column in microsystem technology for a gas chromatograph comprising:
   a first substrate;
   a second substrate which is arranged on the first substrate;
   wherein a trench structure is provided in at least one substrate and the trench structure is sealed off relative to the environment;
   a stationary phase applied at least to parts of the trench structure;
   a gas inlet connected to the trench structure;
   a gas outlet connected to the trench structure; and
   a bonding agent which is at least partly arranged between the walls of the trench structure and the stationary phase, characterized in that the bonding agent is adapted to effect an at least partial electrostatic passivation of the substrate surface in the region of the trench structure, and characterized in that the bonding agent includes a first layer portion and a second layer portion.

2. The separation column as set forth in claim 1 characterised in that the gas inlet and/or the gas outlet is afforded by means of glass capillaries.

3. The separation column as set forth in claim 2 characterised by at least one trench portion which is enlarged in relation to the rest of the trench structure and in which the bonding agent is applied and a glass capillary is fixed as the gas inlet and gas outlet, respectively.

4. The separation column as set forth in claim 1, characterized in that the bonding agent extends over all the walls defining the trench structure.

5. The separation column as set forth in claim 1, characterized in that the stationary phase extends over all the walls defining the trench structure.

6. The separation column as set forth in claim 1, characterized in that the first and/or the second substrate is a silicon wafer or a glass wafer.

7. The separation column as set forth in claim 1, characterized in that the bonding agent includes an inorganic material.

8. The separation column as set forth in claim 1, characterized in that the bonding agent includes a nonpolar material.

9. The separation column as set forth in claim 1, wherein the bonding agent is adapted to effect a complete electrostatic passivation of the substrate surface in the region of the trench structure.

10. A gas chromatograph, comprising:
a separation column comprising:
a first substrate;
a second substrate which is arranged on the first substrate;
wherein a trench structure is provided in at least one substrate and the trench structure is sealed off relative to the environment;
a stationary phase applied at least to parts of the trench structure;
a gas inlet connected to the trench structure;
a gas outlet connected to the trench structure; and
a bonding agent which is at least partly arranged between the walls of the trench structure and the stationary phase,
characterized in that the bonding agent is adapted to effect an at least partial electrostatic passivation of the substrate surface in the region of the trench structure, and
characterized by an electronic control and evaluation unit, and
characterized in that the electronic control and evaluation unit is arranged on a circuit board on which the first substrate of the separation column is arranged at the same time, and
characterized by at least one further circuit board which is arranged in parallel spaced relationship with the first circuit board.

11. The gas chromatograph as set forth in claim 10, wherein the bonding agent is adapted to effect a complete electrostatic passivation of the substrate surface in the region of the trench structure.

12. A process for the production of a separation column comprising the steps:
forming a trench structure in a first substrate,
applying a stationary phase to at least one portion of the trench structure, and
sealing off the trench structure by applying a second substrate,
characterized in that a bonding agent effecting an at least partial electrostatic passivation of the substrate surface in the region of the trench structure is applied to at least parts of the trench structure prior to the application of the stationary phase, and
characterized in that a plasma cleaning or back-sputtering cleaning step is effected between the application of the bonding agent and the application of the stationary phase.

13. The process as set forth in claim 12, characterized in that the bonding agent and the stationary phase are applied to the entire trench structure.

14. The process as set forth in claim 12 characterised in that the bonding agent is formed by means of polymerization of a liquid starting material.

15. The process as set forth in claim 12, characterised in that the bonding agent and/or the stationary phase is applied by means of chemical or physical deposition out of the gaseous phase (PVD or CVD) by means of plasma-aided deposition.

16. The process as set forth in claim 12, characterised in that the bonding agent and the stationary phase are applied by means of an identical process.

17. The process as set forth in claim 16 characterised in that the bonding agent and the stationary phase are applied in a controlled atmosphere, and said atmosphere remains substantially unaltered between the beginning of the application of the bonding agent and the end of the application of the stationary phase.

18. The process as set forth in claim 12, wherein the first substrate, the second substrate, or both, is a silicon wafer.

19. The process as set forth in claim 12, wherein the stationary phase is applied to the trench structure by polymerization of a liquid starting material.

20. The process as set forth in claim 12, wherein the bonding agent is adapted to effect a complete electrostatic passivation of the substrate surface in the region of the trench structure.

* * * * *

UNITED STATES PATENT AND TRADEMARK OFFICE
CERTIFICATE OF CORRECTION

PATENT NO.       : 7,841,225 B2                                         Page 1 of 1
APPLICATION NO.  : 11/665588
DATED            : November 30, 2010
INVENTOR(S)      : Uwe Lehmann It is certified that error appears in the above-identified patent and that said Letters Patent is hereby corrected as shown below:

Column 3
Line 48, "That Inorganic" should read --That inorganic--
Line 50, "Inorganic" should read --inorganic--

Column 4
Line 31, "chromatograph in" should read --chromatograph, in--

Column 9
Line 51, "Information" should read --information--

Signed and Sealed this
Fifteenth Day of February, 2011

David J. Kappos
*Director of the United States Patent and Trademark Office*